United States Patent [19]
Wallshein

[11] 4,379,693
[45] Apr. 12, 1983

[54] ORTHODONTIC BIASSING DEVICE

[76] Inventor: Melvin Wallshein, 8645 Bay Pkwy., Brooklyn, N.Y. 11214

[21] Appl. No.: 104,310

[22] Filed: Dec. 17, 1979

Related U.S. Application Data

[63] Continuation-in-part of Ser. No. 785,587, Apr. 7, 1979, Pat. No. 4,200,979.

[51] Int. Cl.³ .............................................. A61C 3/00
[52] U.S. Cl. ...................................................... 433/7
[58] Field of Search .................... 433/7, 177; 254/204, 254/231, 85, 98, 100, 101, 102, 103, 232, 233, 234, 235, 236

[56] References Cited

U.S. PATENT DOCUMENTS

| | | | |
|---|---|---|---|
| 1,226,830 | 5/1917 | Walker | 254/98 |
| 1,941,378 | 12/1933 | Andrew | 254/98 |
| 3,284,902 | 11/1966 | Dillberg et al. | 433/7 |
| 3,454,001 | 7/1969 | Stockfisch | 433/7 |
| 4,045,871 | 9/1977 | Nelson | 433/7 |

FOREIGN PATENT DOCUMENTS

| | | | |
|---|---|---|---|
| 905056 | 2/1954 | Fed. Rep. of Germany | 433/7 |
| 2722611 | 11/1978 | Fed. Rep. of Germany | 433/7 |
| 831155 | 8/1938 | France | 433/7 |
| 986642 | 8/1951 | France | 433/7 |
| 990685 | 9/1951 | France | 433/7 |
| 998076 | 1/1952 | France | 433/7 |
| 56338 | 9/1952 | France | 433/7 |
| 1206848 | 2/1960 | France | 433/7 |
| 9503 | of 1911 | United Kingdom | 254/231 |
| 718385 | 10/1954 | United Kingdom | 433/7 |
| 335798 | 3/1959 | Sweden | 433/7 |

*Primary Examiner*—Gene Mancene
*Assistant Examiner*—John J. Wilson
*Attorney, Agent, or Firm*—Frishauf, Holtz, Goodman & Woodward

[57] ABSTRACT

Disclosed are various embodiments of orthodontic biassing devices having means for preventing backing-off of the elongated threaded actuating member under reaction forces in the mouth. The backing-off preventing means may comprise angulated or off-set bores for the threaded member and/or guide bars, various means for causing binding up of the guide bars and/or elongated threaded members in the body members, and arrangements wherein the dimensional tolerances are such that one body member may angulate relative to the other body member under force applying conditions to cause binding of the members to thereby prevent backing-off of the threaded member due to reaction forces.

51 Claims, 38 Drawing Figures

FIG. 33

ORTHODONTIC BIASSING DEVICE

CROSS-REFERENCE TO RELATED APPLICATIONS

1. This is a continuation-in-part of my prior application Ser. No. 785,587, filed Apr. 7, 1977, now U.S. Pat. No. 4,200,979.
2. U.S. Pat. No. 3,832,778.
3. U.S. Pat. No. 3,921,294.

BACKGROUND OF THE INVENTION

This invention relates to improved orthodontic screw-type biassing devices, and more particularly to improvements which prevent backing off of the screw which imparts the biassing force.

Prior orthodontic biassing devices of the type to which the present invention pertains generally comprise first and second body members interconnected by a screw member having oppositely threaded ends. As the screw member is rotated, the body members are spread further and further apart, thereby imparting orthodontic biassing forces in the mouth of a patient. The reaction forces against the body members are large, and in some instances are sufficiently high to cause the screw to back off (i.e. rotate in a reverse direction under the influence of the reaction forces applied to the body members), thereby reducing the applied biassing force. The undesirable phenomenon of the screw backing off under the influence of reaction forces applied to the body members is denoted herein as "screw back-off".

The object of the present invention is to provide improved orthodontic biassing devices, of the type discussed above, which substantially prevent or substantially reduce the screw back-off inherent in existing devices.

DETAILED DESCRIPTION

Figure 1:
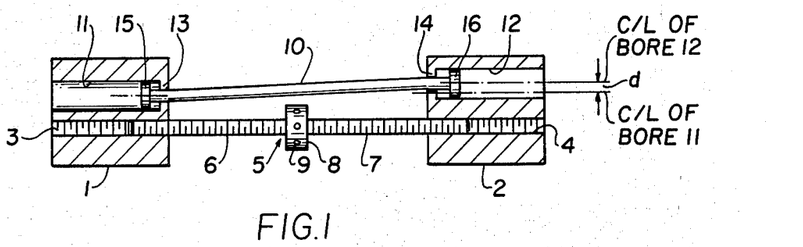
FIG. 1 is a sectional view of a first embodiment of the invention.

FIG. 1 illustrates a first embodiment of the invention comprising respective body members 1, 2 having oppositely threaded bores 3, 4 therein, respectively. A screw member 5 has oppositely threaded portions 6, 7 which are respectively threadably engageable in threaded bores 3, 4. The screw 5 has a spindle portion 8 with engagement recesses 9 for receiving a tool for imparting rotation to the screw 5. A guide bar 10 is provided which is slidably engaged in elongated openings 11, 12 of body members 1, 2, respectively. The elongated openings 11, 12 have respective shoulders 13, 14 therein to prevent passage of the enlarged ends 15, 16, respectively, of the guide bar 10. Typical biassing devices of the type to which the present invention pertains are disclosed in, for example, my U.S. Pat. Nos. 3,832,778 and 3,921,294, and U.S. application Ser. No. 785,587 filed Apr. 7, 1977, the entire contents of which are incorporated herein by reference.

In a first embodiment of the invention, as illustrated in FIG. 1, the elongated threaded bores 3, 4 in the body members 1, 2 respectively, are aligned on the same longitudinal axis and are in line with each other throughout. The bores 11, 12, however, have their center lines laterally off-set with respect to each other, for example by the distance d as indicated in FIG. 1. The illustration of the distance d in FIG. 1 is exaggerated for ease of understanding. The bores 11, 12 are mutually parallel, but are laterally off-set. Therefore, the guide bar 10 will tend to bind in the bores 11, 12 due to the lateral offset of the bores 11, 12. The "binding" of the guide bar 10 in bores 11, 12 is sufficient to prevent or substantially reduce backing off of the screw 5 under the influence of reaction forces. In practice, the lateral offset of the bores 11, 12 may be about 0.001 inches or more, depending upon the length of the device.

Instead of the bores 11, 12 being mutually laterally offset, the bores 11, 12 could be aligned along the same axis and the bores 3, 4 for receiving the screw 5 may be laterally offset. See FIG. 2. This will also produce the desired "binding" effect to prevent backing off of the screw 5 under the influence of reaction forces. The off-set d' illustrated in FIG. 2 may be similar in dimensional range to the off-set d illustrated in FIG. 1 and described in the paragraph immediately above.

Figure 3:
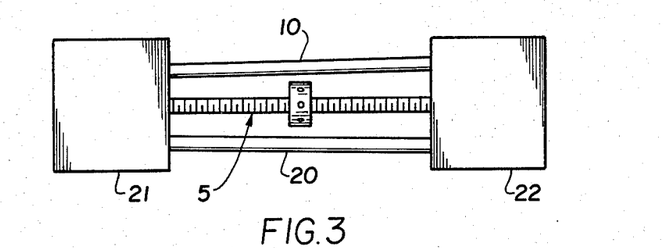
FIG. 3 is a plan view of a third embodiment of the invention.
Figure 4:
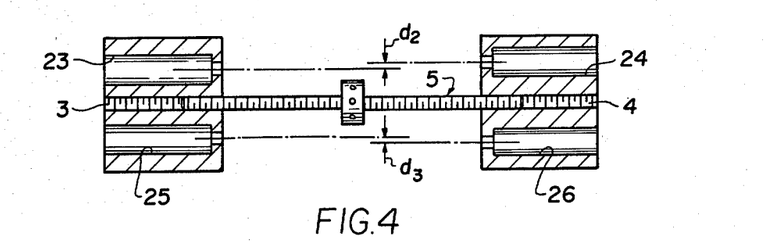
FIG. 4 is a plan view of another embodiment of the invention.

FIG. 3 illustrates a further embodiment of the invention comprising two guide bars 10, 20 with a screw 5 located therebetween. The body members 21, 22 are illustrated in FIG. 4 in cross-section. In FIG. 4, the threaded bores 3, 4 are mutually aligned on the same longitudinal axis. However, the bores or openings 23, 24 have their longitudinal axes offset by a distance $d_2$. The longitudinal axes of the openings 25, 26 for guide bar 20 are offset by a distance $d_3$. In the FIG. 4 embodiment, the offsets of the longitudinal axes of the bores 23–26 are such that the guide bars 10, 20 are angulated in a direction to converge toward the left hand side of the device in FIG. 4. This provides the desired "binding effect" to prevent backing off of the screw. The dimensional ranges of the off-sets $d_2$ and $d_3$ in FIG. 4 may be within the ranges discussed above with respect to FIG. 1.

As an alternative, the longitudinal axis of the bore 25 may be below that of the bore 26 (opposite to the orientation shown in FIG. 4). This will also provide the desired binding effect.

In addition, referring to the embodiment of FIG. 4, the threaded bores 3, 4 may be off-set (as in FIG. 2) to increase the binding effect. Again, the degree of off-set may be within the ranges discussed in the embodiment of FIGS. 1 and 2.

Figure 5:
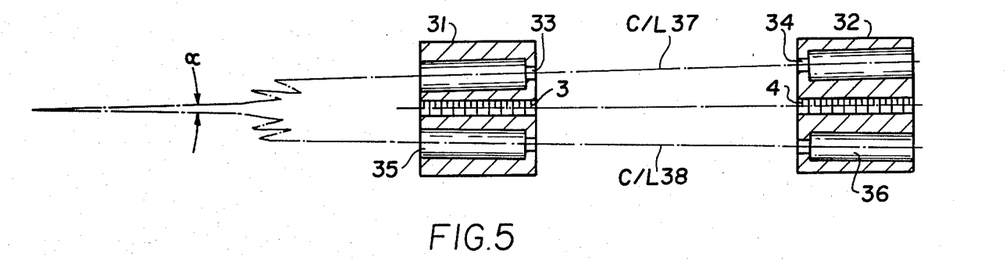
FIG. 5 is a plan view of still another embodiment of the invention.

Instead of off-setting the bores which receive either the screw of guide bars, some of the bores may have longitudinal axes which are aligned, but which are at an angle to the longitudinal axes of the other bores. One such embodiment of this concept is illustrated in FIG. 5. In FIG. 5, the threaded bores 3, 4 are mutually aligned and have the same center line. The bores 33 and 34 have the same center line, but the center line thereof is angulated relative to the center line of bores 3, 4. Bores 35, 36 are aligned on the same center line, their center line being also angulated with respect to the center line of the bores 3, 4. In FIG. 5, the angle between the center lines 37, 38 is indicated to be $\alpha$. $\alpha$ may be several degrees, for example 1° or 2°, and preferably lies within the range of from about ½° to about 3° or 4°. The bores 33, 34 receive a common guide bar, such as guide bar 10 and the bores 35, 36 receive another common guide bar. As the body members 31, 32 are spread apart by operation of the screw 5 (threaded in bores 3, 4), the angulation of the bores for the guide bars will cause binding which will prevent or substantially reduce backing off of the screw due to reaction forces. The angle $\alpha$ in FIG. 5 is greatly exaggerated for ease of illustration and understanding.

Figure 2:
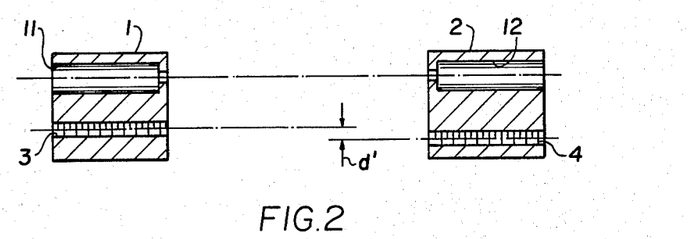
FIG. 2 is a sectional view of a portion of a second embodiment of the invention.

While FIG. 5 illustrates two sets of bores for two respective guide bars, one angulated set of bores could be used. Instead of the bores for the guide bar or bars being angulated, the bore for the threaded screw could be angulated. The critical feature is that the bores for the guide bars and screw be angulated relative to each other, or at least one set of bores comprising a pair of off-set bores, as illustrated in FIGS. 1–3.

Figure 6:
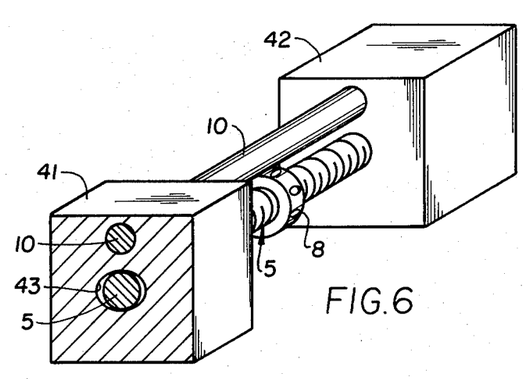
FIGS. 6 and 6A-6C are views of further embodiments of the invention.

FIG. 6 illustrates another embodiment of the invention for preventing backing off of the screw 5. In FIG. 6, the threaded bore 43 for receiving the threaded portion of the screw 5 is deformed, for example by squeezing, pressing or otherwise deforming the body member 41 so that the screw 5 is very tightly received in the threaded bore 43 so that it effectively binds and prevents backing off of the screw due to reaction forces. The screw is capable of being turned, however, under the force of a tool inserted in the openings 9 of the spindle 8 thereof (see FIG. 1). The deformity of threaded bore 43 is exaggerated in FIG. 6 for ease of illustration. In FIG. 6, the bore 43 is deformed throughout its entire length. The threaded bore 43 in one or both of blocks 41 and 42 may be so deformed.

In an alternative arrangement, the bore 43 of FIG. 6, instead of being deformed, is threaded with slightly undersized threads relative to the threads of the screw 5 so that it is difficult to thread the screw 5 into the threaded bore 43. The difficulty of threading is sufficient to prevent backing off of the screw due to reaction forces, but is not sufficient to prevent positive feeding of the screw into the bore under the influence of a tool on spindle 8 to provide desired biassing forces. Rather than provide undersized threads in bore 43, threads of a slightly different thickness can be used in bore 43 to provide the desired frictional fit or tightness to prevent backing off of the screw.

Figure 6A:
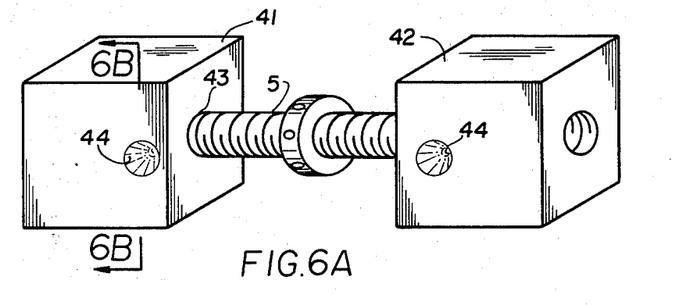
Figure 6B:
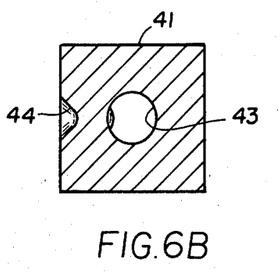

FIG. 6A illustrates a modified embodiment similar to that of FIG. 6 wherein only a portion of body member 41 and/or body member 42 is deformed to deform only a portion of the length of the threaded bores 43 in the body members 41 and/or 42. FIG. 6A illustrates the deformation by means of a "dimple" which is, for example, punched or formed by impacting, the respective body member with sufficient force to deform at least a portion of the threaded bore 43 to cause the threads thereof to frictionally bind with the threads of the screw member 5. In FIG. 6A, dimples 44 are shown on each of the blocks 41, 42. FIG. 6B shows a cross-sectional view of block 41 in the vicinity of the dimple 44, showing the deformation of the portion of threaded bore 43 opposite dimple 44 in an exaggerated manner for ease of illustration.

Figure 6C:
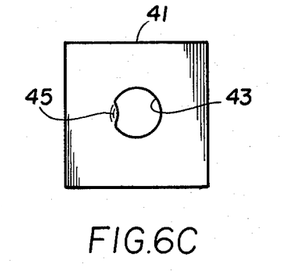

FIG. 6C illustrates another embodiment of the invention where only the opening portion of the threaded bore 43 at the point where the screw member 5 enters, is deformed, either by means of a dimple similar to dimple 44 being formed at the leading edge portion of the body member 41, or by other equivalent means, for example impacting or otherwise deforming body member 41 in the vicinity of the opening of threaded bore 43. The deformation 45 of bore 43 is shown in an exaggerated manner in FIG. 6C for ease of illustration. The body member 42 may also or alternatively be so deformed as shown in FIG. 6C.

Figure 7:
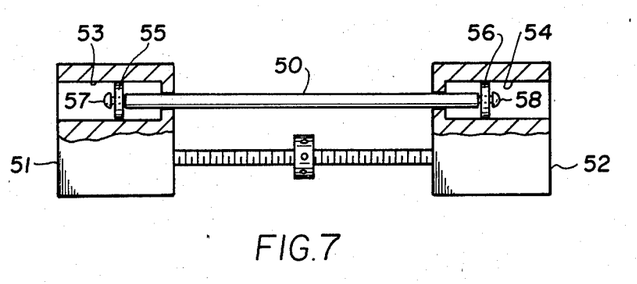
FIG. 7 is a sectional view of still another embodiment of the invention.

FIG. 7 illustrates another embodiment of the invention wherein the guide bar 50, which is slideably engaged in bores 53, 54 of body members 51, 52, respectively, has precisely dimensioned washer-like members 55, 56 at the opposite ends thereof. Washers 55, 56 are mounted on reduced diameter end portions of the guide bar 50, the reduced diameter end portions being then deformed or otherwise turned over at 57, 58 to retain the washers at the ends of guide bar 50. Due to the close dimensional tolerances and the precise fit between the washers 55, 56 and the respective bores 53, 54, if backing off forces are applied to the body members 51, 52, such backing off forces tend to tilt or otherwise misalign the body members 51, 52 which causes the respective washers 55, 56 to bind in their precisely mated respective bores 53, 54. The washers 55, 56 may be made slightly oversized so as to provide drag in the bores 53, 54, the drag being low enough to permit operation of the device by means of a tool on spindle 8, but high enough to prevent backing off of the screw due to reaction forces.

Figure 8:
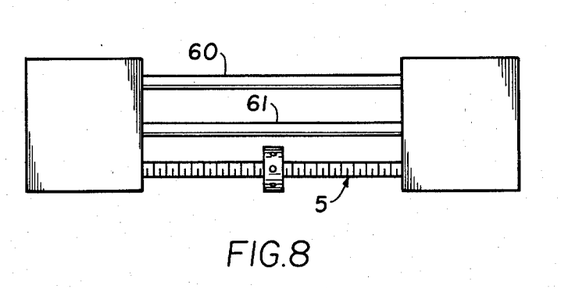
FIG. 8 is a plan view of yet another embodiment of the invention.

FIG. 8 illustrates another embodiment of the invention comprising two guide bars 60, 61 mounted on the same side of the actuator screw 5. This construction is advantageous in that it exposes the actuator screw 5 so that it is more easily adjusted in the mouth of a patient. If guide bars are placed on opposite sides of the actuator screw 5, as in FIG. 3, it is more difficult for the operator to actuate the screw by engaging a tool in its spindle 8. In the embodiment of FIG. 8, the bores for the guide bars and/or screw 5 may be off-set, angulated, in any combination, to provide the desired backing off prevention of the screw 5. Moreover, the threaded bore for the screw 5 may be deformed as shown in FIG. 6 and FIGS. 6A-6C and discussed above.

Figure 9:
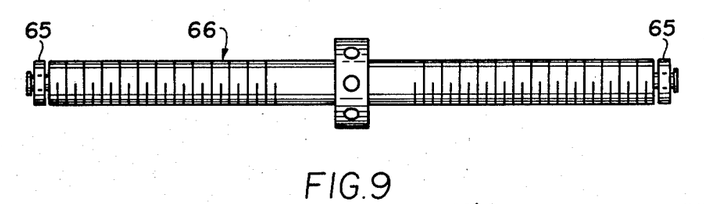
FIGS. 9 and 9A illustrate actuating screws according to embodiments of the present invention.

FIG. 9 illustrates a further embodiment of the invention in which a washer-like member 65 is mounted to the respective opposite ends of the actuator screw 66 in substantially the same manner as the washers 55,56 are mounted to the guidebar 50 in FIG. 7. The operation of the washer-like members 65 in FIG. 9, which fit into precisely dimensioned threaded bores in the body housings, is substantially similar to the embodiment of FIG. 7. Due to the close dimensional tolerances, and the precise fit between the washer-like members 65 and the threaded bores in which the actuator screw 66 is threadably inserted, the washer-like members 65 act to substantially prevent backing off of the actuator screw due to reaction forces.

The washers at the end of the actuator screw 66 can be used in conjunction with corresponding washers at the ends of the guidebars (FIG. 7) to further enhance performance. Additionally, in FIG. 8, any or all of the guidebars 60,61 and actuator screw 5 may include washer-like member of FIGS. 7 and/or 9 to enhance prevention of backing off of the screw due to reaction forces.

Figure 9A:
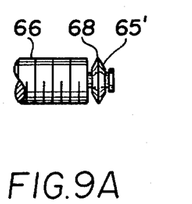

FIG. 9A illustrates a modified embodiment of the actuator screw arrangement of FIG. 9. The washer-like member 65' of FIG. 9A has rounded or pointed peripheral ends 68 which engage between adjacent threads of the threaded bore, for example threaded bores 3, 4 in FIG. 1, of the body members into which the threaded actuator screw is received. The pointed or rounded peripheral portions 68 are dimensioned to frictionally or interferingly engage the adjacent threads to produce a drag or friction fit against which the actuator screw is actuated. The drag is high enough to substantially prevent backing off of the actuator screw 66 due to reaction forces, but is low enough to permit the actuator screw 66 to be rotated in its operating direction by means of a tool inserted into the spindle thereof. Alternatively, the washer-like member 65, 65' of FIGS. 9 and 9A, respectively, can be replaced by washer-like members such as those shown in FIGS. 10-14 and which are described in greater detail below.

Figure 10:
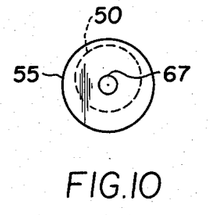
FIGS. 10 and 11 are end views of still further embodiments of the invention.
Figure 11:
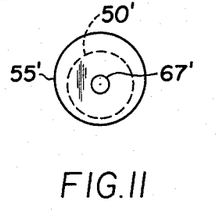

FIG. 10 illustrates a modified embodiment wherein the washer-like member 55,56 (FIG. 7) is eccentrically mounted to a guide bar 50. The washer-like member 55 is mounted to a turned down portion 67 at the end of the guide bar 50, the end of the turned down portion being peened over or otherwise deformed to maintain the washer-like member 55 in position, as shown for example in FIGS. 7 and/or 9. FIG. 11 illustrates a similar embodiment wherein the washer-like member 55' is eccentric relative to the mounting hole thereof and is mounted to a non-eccentric turned-down portion 67' of a guidebar 50'. The net result is similar in effect as obtained with the embodiment of FIG. 10. Adequate binding is obtained in both cases.

Figure 12:
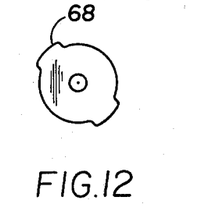
FIGS. 12, 13 and 14 illustrate further modifications of the embodiments of FIGS. 10 and 11.

The embodiments of FIGS. 10 and 11 can be applied to the embodiment of FIG. 9. By having the eccentric washer-like member or an eccentrically mounted washer-like member, a small contact surface is provided with the bore in which the member is mounted, thereby enhancing backing-off prevention. Instead of eccentricity, the washer-like member may be formed with projections 68 thereon, such as shown in FIG. 12. The projections 68 are dimensioned to bear on the bore in which they are inserted with sufficient force to provide drag which can be overcome by turning of the actuator screw, but with sufficient drag to substantially prevent backing-off of the screw due to reaction forces.

Figure 13:
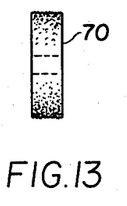
Figure 14:
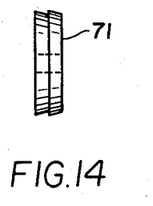

The washer-like member may have rough outer edges 70 as shown in FIG. 13 to enhance backing-off prevention. The outer edges of the washer-like member may be serrated as shown at 71 in FIG. 14. This arrangement facilitates one-way movement of the washer-like member and provides gripping surfaces to more effectively prevent backing-off. The washers of FIGS. 12-14 can be utilized at the ends of guide bars and/or actuator screws, as should be apparent from the foregoing discussions. The washers of FIGS. 13 and 14 are particularly advantageous when used in threaded bores as in FIGS. 9 and 9A since they better engage the threads due to their irregular outer surfaces.

Figure 15:
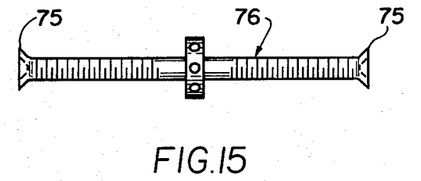
FIG. 15 illustrates a further actuating screw according to the present invention.

FIG. 15 illustrates a further embodiment of the invention wherein the ends of the actuator screw 76 are turned or spun outwardly to act as means for preventing the actuator screw from becoming unthreaded for the body housing in which it is mounted. Due to tolerances in the construction, play between the members causes the outwardly spun ends 75 of the actuator screw 76 to bind in the bore in which the actuator screw is mounted, thereby preventing backing off of the actuator screw due to reaction forces. The ends 75 of the actuator screw are spun out, for example by spinning the actuator screw on a lathe and applying a sharp or slightly pointed tool against the ends of the actuator screw 76 at approximately the longitudinal axis thereof to cause the end portions to become spun out or circumferentially deformed, as illustrated at 75 in FIG. 15. The outwardly deformed ends 75 are shown in an exaggerated manner in FIG. 15—in practice they do not protrude outwardly much further than the most inward peaks of the threaded bore into which the screw is threaded. A drag is thus produced between the ends 75 of the screw and the threaded bore into which the screw is threaded.

Figure 16:
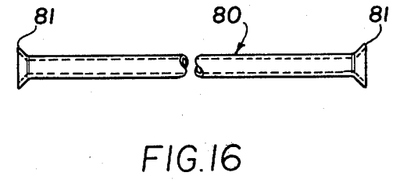
FIGS. 16 and 17 illustrate guide bar arrangements according to the present invention.
Figure 17:
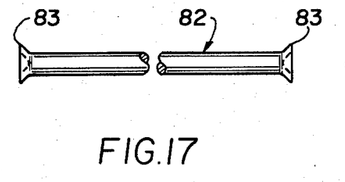

FIG. 16 illustrates an embodiment of a guidebar 80 (used and mounted similarly to guidebar 50 of FIG. 7) with spun out ends 81. The spun out ends serve to retain the guidebar in the body housings and, similarly to the washers 55,56 of FIG. 7, bind on the inner walls of the bores 53,54 of the body housings 51,52, respectively, of FIG. 7. The ends of the guide bar are spun out at 81 in a manner similar to that discussed above with respect to FIG. 15. In FIG. 16 the guidebar 80 is shown as a hollow tube. FIG. 17 illustrates a similar guidebar 82 in the form of a solid tube with spun out ends 83 which are spun out or circumferentially deformed in a manner similar to that described with respect to the spun out ends 75 of FIG. 15.

Figure 18A:
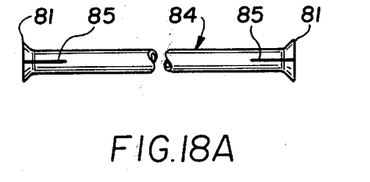
FIGS. 18a and 18b illustrate modified guide bars according to the present invention.
Figure 18B:
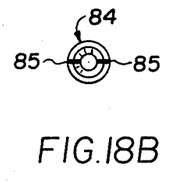
Figure 19:
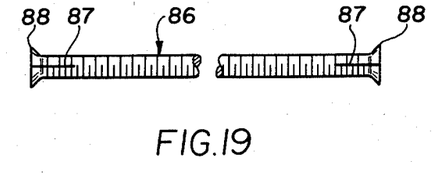
FIG. 19 shows an actuator screw modified in a similar manner as the guide bar of FIGS. 18A and 18B.

FIGS. 18A and 18B illustrate a modified guide bar 84 which is illustrated as being hollow (similar to guide bar 80 in FIG. 16), but which has longitudinal splits or cuts 85 formed in the end portions thereof. The end portions 81 thereof are sprung slightly outwardly and resiliently bear against the inner surface of the guide bar receiving bores of the respective body members. The resilient engagement in the guide bar receiving bores is provided due to the natural springiness of the metallic material from which the guide bars 84 are made. The split 85 may be formed in the end portions of the solid guide bar 82 of FIG. 17 to provide similar improved results. Similarly, the ends of a threaded actuator screw may be outwardly flared and split as shown in FIG. 19. The actuator screw 86 in FIG. 19 is only partially shown, the end portions thereof having splits or cuts 87 therein to provide the springy, resilient engagement of the end portions 88 of the actuator screw 86 within the threaded bores of the respective body members. This arrangement is particularly advantageous since the springiness at the ends of the threaded screw member cause substantially one-way engagement or locking with the threads in the threaded bores due to the end portions of the flared out portions 88 engaging in threads. This is a generally ratchet-type arrangement which provides excellent backing-off prevention characteristics.

Figure 20:
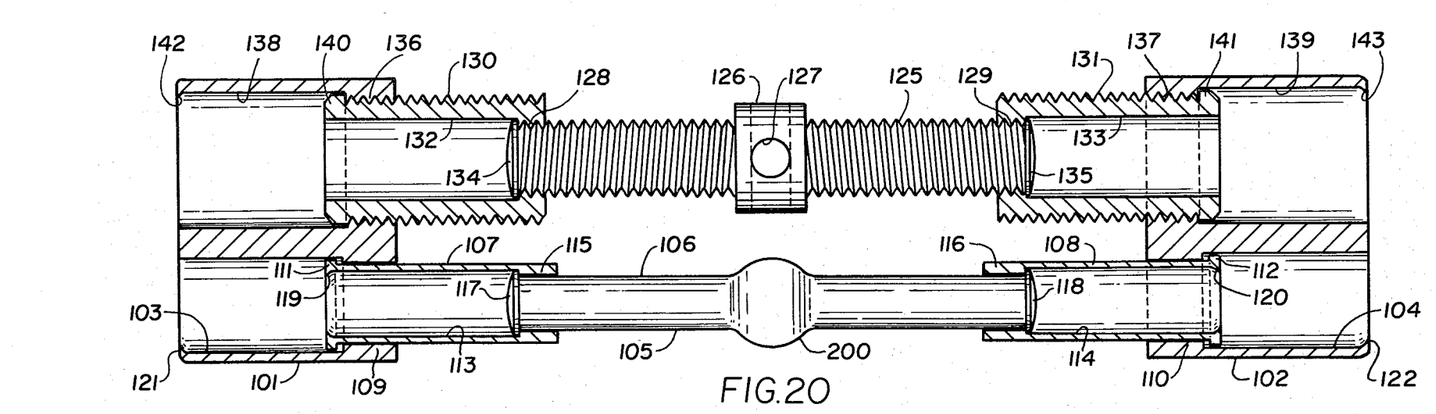
FIG. 20 is a sectional view of yet another embodiment of the invention

FIG. 20 illustrates a further embodiment of the invention which is particularly advantageous in practice. Body members 101, 102 have respective bores 103, 104 therein for slideably receiving a telescoping guide bar or pin 105. Guide bar 105 comprises a central section 106 which is telescoping with respect to opposing end sections 107, 108. End sections 107, 108 are telescopingly received in the bores 103, 104, respectively, of body members 101, 102. Bores 103, 104 have necked-down or reduced diameter front portions 109, 110, respectively, and end sections 107, 108 have flange portions 111, 112, respectively which abut against reduced diameter portions 109, 110. End sections 107, 108 have respective bores 113, 114 therein and respective reduced diameter forward portions 115, 116. Central guide bar section 106 has flanges 117, 118 at the opposing ends thereof which are slideable in respective bores 113, 114, and which abut against respective reduced diameter sections 115, 116. End sections 107, 108 have further reduced diameter rear portions 119, 120 to prevent the central section 106 from protruding out of the rear end of the biassing device when the device is collapsed, for example by turning in the actuating screw. Body members 101, 102 have respective reduced diameter or abutment end portions 121, 122 to prevent the end sections 107, 108 from protruding rearwardly of the device when it is collapsed.

The embodiment of FIG. 20 further comprises a telescoping screw arrangement with a central screw member 125 having an actuating spindle portion 126 with a tool receiving opening 127 for receiving a tool for imparting rotation to screw 125. The central screw section 125 is threaded with oppositely directed threads on the respective opposite ends of spindle 126. Threaded screw member 125 is threadably received and threaded bores 128, 129 of telescoping end members 130, 131. End members 130, 131 have enlarged bore portions 132, 133 through which enlarged flange portions 134, 135 of screw member 125 may slideably pass. The enlarged flange portions 134, 135 abut against the threaded portions 128, 129 to limit the forward movement of screw member 125 relative to telescoping threaded members 130, 131. Telescoping members 130, 131 have threaded outer surfaces which engage threaded bore portions 136, 137 of body members 101, 102, respectively. Body members have enlarged bore portions 138, 139 extending rearwardly of respective threaded portions 136, 137 through which enlarged flange portions 140, 141 of telescoping members 130, 131 may slideably pass. Body members 101, 102 have inwardly projecting portions or enlargements 142, 143 to abut against the rear portions of telescoping members 130, 131 to prevent them from projecting rearwardly of the body members when the device is being collapsed.

In order to prevent the screw members 125, 130, 131 from "backing off" when pressure is applied to teeth in the mouth, the various screw engagements and the clearances between the various enlarged ends of the screw members and guide pin members are designed with clearances or loose tolerances so that the members have slight wobble with respect to each other. Due to the slight "wobble" with respect to the adjacent contacting members, the members "bind" relative to each other to substantially prevent backlash. In other words, when the members bind, it is due to the bending moments applied to the device about its longitudinal axis due to the reaction forces of the teeth in the mouth, thereby causing misalignment and binding due to the tolerances between adjacent sliding parts.

In the embodiment of FIG. 20, it should be clear that some of the sliding tolerances could be tight, and some could be loose. The important feature is that at least some of the tolerances between adjacent sliding parts are loose enough so that sufficient wobble is produced so that the parts tend to go out of alignment due to reaction forces in the mouth, thereby causing the device to "bind" and to prevent backing off of the screw members relative to the body members due to reaction forces in the mouth.

The central section 106 of the telescoping guide bar may be deformed for example at 200 to create outwardly extending "dimples". When the body members 101,102 are contracted the dimple 200 bears against the forward ends of end sections 107,108 to prevent too long a portion of central member 106 from extending into the end sections 107,108. Thus, the central member 106 is prevented from extending beyond the rear end of end sections 106,107 and likewise is prevented from extending from the rear ends of the body members 101,102 when the body members are contracted. By providing the dimple or deformation 200, the reduced diameter rear portions 119,120 on end sections 107,108 may be eliminated. If desired, both the reduced diameter end portions 119,120 and the dimple 200 can be provided to provide more reliable operation.

Figure 21:
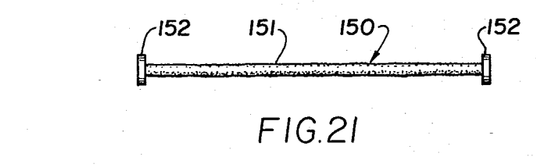
FIG. 21 illustrates a guide bar of the present invention.

FIG. 21 illustrates a further embodiment of the invention wherein a guide pin or bar has a roughened or serrated outer surface 151 which creates increased friction against the bearing surfaces of the body members into which the guide pin 150 is slideable. For example, in the embodiment of FIG. 1, the serrated or roughened surface 151 cooperates with shoulders 13,14 of body members 1, 2, respectively to increase friction therebetween and to enhance the backing-off preventing effects. In FIG. 21, the ends of guide pin 150 have enlarged end portions 152. However, the enlarged end portions 152 may be replaced by washer-like members, for example as illustrated with respect to FIGS. 9-14, could have flared ends as illustrated in FIGS. 16 and 17 and/or could have flared split ends as illustrated in FIGS. 18 and 19. The serrated or roughened surface 151, in combination with the aforementioned backing-off prevention means at the ends of the guide pin or bar 150, provides improved effects.

Figure 22:
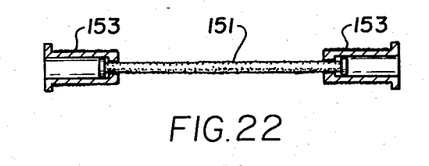
FIG. 22 illustrates a telescoping guide bar using the concepts of FIG. 21.

FIG. 22 illustrates a telescoping guide pin or bar utilizing the concept of FIG. 21 and is self-explanatory.

The serrated surfaces 151 and 153 cooperate with the shoulders through which they slide to increase friction and to further prevent backing-off. The guide pin of FIG. 22 is particularly suitable for use in the overall arrangement of FIG. 20, as well as in the angulated or off-set center line arrangements discussed hereinabove.

Figure 23:
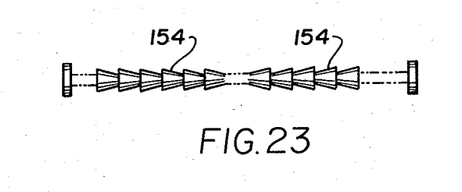
FIGS. 23 and 24 illustrate modified guide bars of the present invention.

Instead of being of roughened or serrated in a random matter as illustrated in FIGS. 21 and 22, the surfaces of the guide pin may be serrated in a one-way direction to enhance prevention of backing-off, for example as illustrated in FIG. 23. In FIG. 23, the serrations 154 are shown enlarged for ease of illustration. The ratchet or tooth-type serrations 154 are oppositely directed on opposite sides of the guide pin for proper cooperation with the respective body members. The embodiment of FIG. 23 can be implemented in the arrangement of FIG. 22, as should be apparent. In this instance, the serrations 151,153 would be replaced by properly directed tooth or ratchet-type serrations 154.

Figure 24:
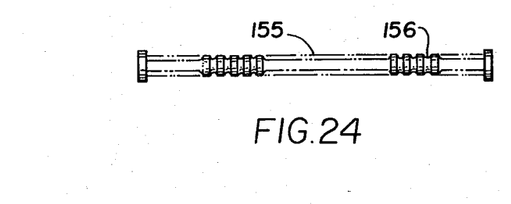

FIG. 24 shows another arrangement wherein the surface 155 of the guide bar or pin is formed with depressions 156 therein. The depressions 156 define a roughened or serrated-type surface which also prevents prevents backing-off of the body members, such as body members 1,2 or the other body members illustrated in the drawings. Again, the surface configuration shown in FIG. 24 can be applied to the arrangement shown in FIG. 22, as should be apparent.

Figure 25:
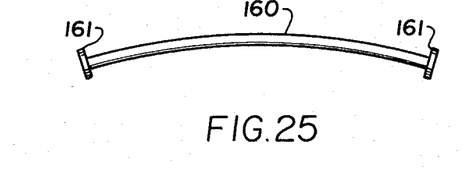
FIGS. 25-27 illustrate guide bars of the present invention which are longitudinally deformed in accordance with the present invention.
Figure 26:
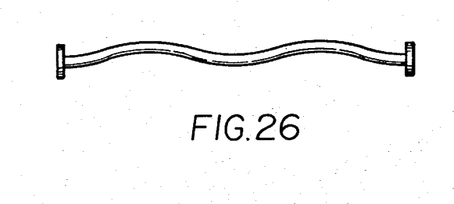
Figure 27:
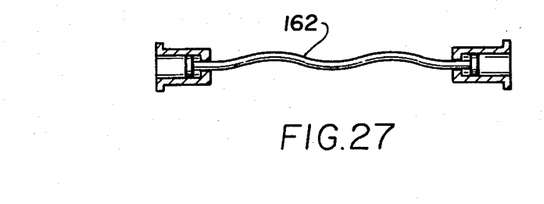

FIG. 25 illustrates a further guide bar 160 which is longitudinally distorted, for example in the shape of an arc, to provide backing-off prevention means. This arrangement has a similar effect as angulating bores as shown in FIG. 5, or laterally off-setting center lines of opposed bores, as shown for example in FIGS. 1, 2 and 4. As the body members are screwed apart, and the enlarged ends 161 of guide bar 160 are engaged in the bores, such as bores 11,12 in FIG. 1, the curved portion 160 of the guide pin will engage, for example shoulders 13,14 with a relatively high friction, the frictional forces being low enough so that the body members may be separated by means of the tool engaging the spindle 8 of the screw, but high enough to prevent backing-off of the body members due to reaction forces of the teeth. The curved guide pin of FIG. 25 need not necessarily be curved as illustrated in FIG. 25—it may be tortuously curved as illustrated for example in FIG. 26. It should be clear that the degree of curvature in FIGS. 25 and 26 is exaggerated for each of illustration. Also, the curvatures of the guides pins in FIGS. 25 and 26 may be applied to the central guide bar 105 in the embodiment shown in FIG. 20, wherein the guide bar is a telescoping guide bar. Such an embodiment is illustrated, for example, in FIG. 27. In FIG. 27, the curvature illustrated in FIG. 26 is used for the central guide bar 162. The curvature shown in FIG. 25 could be used instead.

Figure 28:
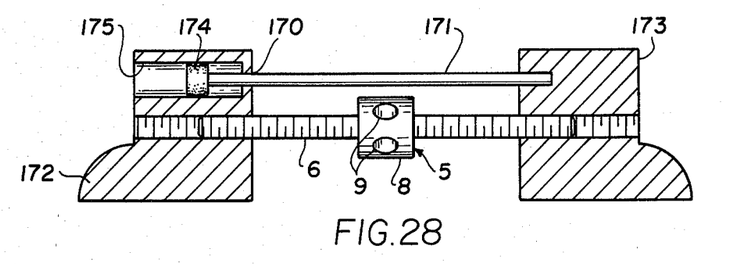
FIG. 28 illustrates yet another modified arrangement of the present invention.

FIG. 28 illustrates another embodiment of the invention wherein the guide bar 171 is slideable in the opening of a shoulder 170 of body member 172. The other end of the guide bar 170 is fixed in body member 173. The free end 174 of the guide bar 171 is enlarged and has its surface rough or serrated so as to tightly fit in the bore 175 of body member 172. The enlarged end 174 is dimensioned to tightly fit in bore 175 and the roughened outer surfaces thereof provide sufficient drag or friction so that the body members 172,173 may be easily separated by rotating spindle 8 of screw 6, but prevents backing-off of the screw due to reaction forces. The bar 171 of FIG. 28, which is fixedly mounted in one of the body housings, may have a washer-like member at the end thereof, for example as shown in FIGS. 10–14, may be flared and/or split as shown in FIGS. 16, 17, 18 and 19, may have a roughened surface over the main length thereof, for example as shown in FIGS. 21, 23 and 24, or may be curved as shown in FIGS. 25 and 26. Various of the above characteristics can be imparted to the bar 171, in combination, as desired. Still further, the various bores of the body members 172,173 in FIG. 28 may be off-set or angulated, as discussed with respect to FIGS. 2, 4 and/or 5.

Figure 29:
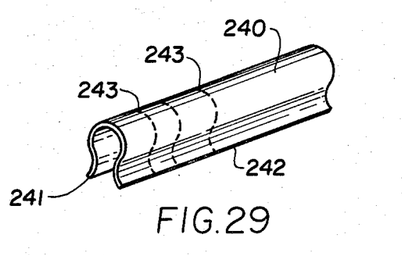
FIGS. 29 and 30 illustrate yet another means for preventing backing off of a threaded screw member.
Figure 30:
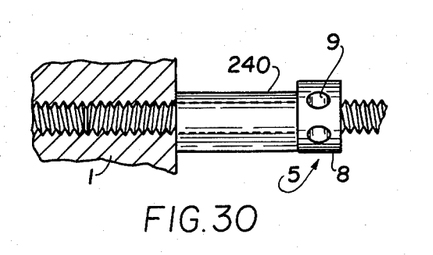

FIGS. 29 and 30 illustrate a further means for preventing backing-off of the screws into the body members due to reaction forces. As shown in FIG. 29, the backing-off preventing means comprises an elongated generally U-shaped member 240 which is adapted to be snapped or fit over a screw to retain it in position relative to a body member. The sleeve or member 240 is preferably made of a material which permits flexing thereof as the ends 241,242 are pressed over an expansion screw and snapped into place on the expansion screw. The ends 241,242 are flared outwardly to facilitate snapping the member 240 over a screw. The member 240 may be made of a spring metal, relatively rigid and flexible plastic material, or the like. When it is made of plastic material, it must have sufficient strength in its longitudinal direction to prevent the reaction forces due to pressure of the teeth from causing the screw to back into the body member. The member or sleeve 240 may have weakened areas 243 at which it may be snapped off to adjust same to the desired length. Alternatively, the length of the member 240 may be varied by snipping same off with a cutting implement, such as scissors, diagonal cutters, or the like.

FIG. 30 illustrates the sleeve 240 snapped into place over a screw 5 of the expansion device and interposed between the spindle 8 and a body member 1. If desired, to improve reliability, a similar member 240 may be installed on the other side of the spindle 8 and the other body member (not shown), for example body member 2 in FIG. 1. Still further, if desired, the member 240 may be made large enough to snap over the spindle 8 and to span the distance between the body members, such as body members 1,2 of FIG. 1, to achieve substantially the same result by bearing against the respective body members to prevent backing-off of the screw.

Figure 31:
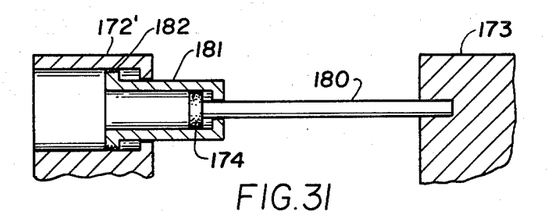
FIG. 31 illustrates a modified arrangement along the lines of the embodiment of FIG. 28.

FIG. 31 illustrates a modified embodiment of the arrangement shown in FIG. 28. The guide bar 171 of FIG. 28 is replaced in FIG. 31 with a two-piece telescoping guide bar arrangement comprising guide bar 180 which is fixedly mounted in body member 173 and a telescoping member 181 which is slideably mounted in body member 172′, the fixed bar 180 being slideably mounted in member 181. The end 174 of the bar 180 may be roughened or serrated, as shown in FIG. 28, as may be the end 182 of member 181. Any of the other means discussed hereinabove can be used on the guide pin 180 and member 181 for preventing backing-off of the screw member. The screw member is not shown in FIG. 31 for ease of illustration. Moreover, the two-piece telescoping arrangement of FIG. 31 may be used in any of the other expansion devices discussed hereinabove.

In FIG. 31, the right side of bar 180 is fixedly mounted in body member 173. The right side, however, can be freely slideably mounted in a bore in body member 173, in a manner similar to the embodiment shown in FIG. 1. Thus, a completely slideably mounted two-piece telescoping guide bar, with appropriate retention and backing-off prevention means, is provided. Again, in such an arrangement, any of the backing-off prevention means discussed hereinabove can be used in connection with guide bar 180,181.

Figure 32:
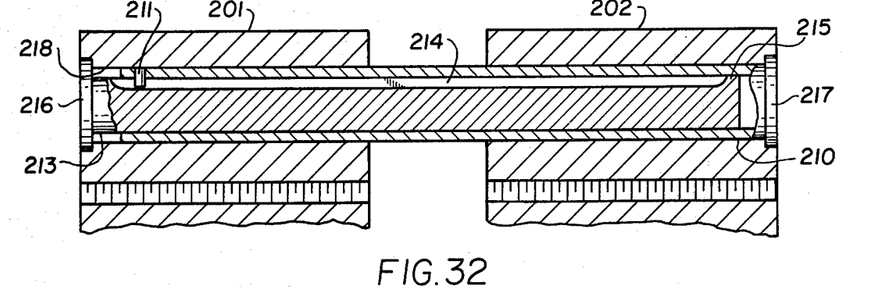
FIG. 32 illustrates yet another embodiment of the invention.

FIG. 32 illustrates another embodiment of the invention wherein body members 201,202 (only partially shown) have threaded bores, as illustrated in FIG. 32, for receiving a threaded actuating screw with oppositely threaded ends. The actuated screw is not shown in FIG. 32 for ease of illustration. Fixedly connected to body member 201 is an elongated guide bar member 213. Guide bar member 213 has an enlarged head portion 216 for ease of assembly, although the head portion 216 need not be provided. Fixedly connected to body member 202 is a hollow guide tube 210 which extends through the body member 202 and is connected to the end thereof by means of an enlarged head member 217. Again, head member 217 need not be provided. It provides for ease of installation. Guide bar 213 is slideably engaged in guide tube 210. Body member 201 has a bore 218 therein which is larger than the diameter of guide bar 213 so that guide tube 210 may nest within bore 218 of body member 210, as shown in FIG. 32. Upon expansion of the body members 201,202, the guide tube 210 is pulled out of the bore 218 in body member 201. Guide bar 213 has a longitudinal groove 214 therein with an enlarged end portion 215. When the guide bar and guide tube become fully disengaged, the enlarged end portion 215 abuts against pin 211 to prevent complete disengagement of the assembly. Other abutment means can be used to replace the pin 211, groove 214 and enlarged end portion 215. For example, guide bar 213 may take the general shape of guide bar 180 of FIG. 31 and the guide tube 210 may take the general shape of member 181 in FIG. 31, the left-most end of member 181 in FIG. 31 being fixed to the body member 202 in the same manner as shown in FIG. 32. In this case, the enlarged end 174 and the reduced diameter portion of member 181, shown in FIG. 31, acts as the abutment means to prevent disengagement of the guide bar arrangement.

In FIG. 32, the tolerances between the guide bar, guide tube and bore in body member 201 may be loose so that that the various members can angulate relative to each other and bind to prevent backing-off of the screw member due to the influence of reaction forces in the mouth. Other backing off preventing means, such as discussed hereinabove but with respect to any and all of the other figures, and which are compatible with the embodiment of FIG. 32, may be used.

As backing-off preventing means in connection with the elongated threaded members, the threaded members may be provided with threads which are either loose relative to the members they engage to permit the threaded members to angulate relative to each other (when they are telescoping) and/or relative to their respective body members. The angulation which occurs due to reaction forces causes the members to bind in the reverse direction to prevent backing-off of the elongated threaded member due to the reaction forces. The binding, however, is insufficient to prevent rotation of the threaded members in the forward or expanding direction, but is sufficient to prevent backing-off. Instead of providing loose threaded connections, oversized threads may be used to provide an "interfering fit", the interference being sufficient to provide enough friction to prevent backing-off, but being low enough to permit the threaded members to be actuated in the forward direction with a manual tool, or the like. Instead of oversized threads, different sized threads (such as different pitches, different thread thicknesses, etc.) can be used to provide the appropriate interference fit.

Figure 33:
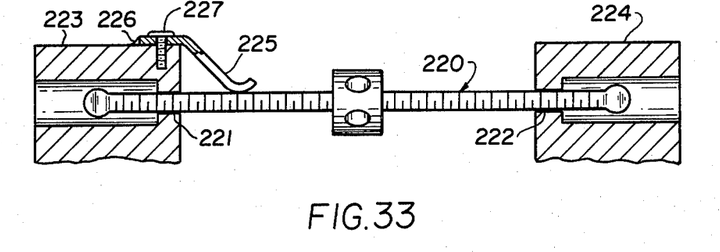
FIG. 33 illustrates yet another embodiment for preventing backing off of a threaded screw member.

FIG. 33 illustrates another means for preventing backing off of the threaded member 220 which is threadably engaged in respective threaded bores 221, 222 of body members 223, 224. The body members 223, 224 are only partially shown—they may include guide bars, etc. as illustrated in the other Figs., as desired. In accordance with the invention, a spring 225 projects from body member 223 and springingly bears on a surface of threaded member 220 to apply pressure to threaded member 220. The pressure applied by spring member 225 is sufficient to increase the frictional engagement between the threaded member 220 and its associated threaded bores 221, 222 to prevent backing off of the threaded member 220 due to reaction forces in the mouth. The spring member 225 may be made of wire or flat spring metal, or even plastic material having the necessary resilient characteristics to apply pressure to the threaded member 220. Spring member 225, when made of metal, may be welded to a body member 223, for example at 226, or may be riveted or screwed to the body member by means of a rivet or screw 227.

While FIG. 33 shows only one spring member 225, another spring member may be applied to body member 224. Moreover, spring members such as spring member 225 may be applied against a guide bar from one or both body members to resist backing off of the threaded member 220 due to reaction forces.

The various features discussed above may be combined in various compatible combinations.

I claim:
1. An orthodontic biassing device comprising:
two body members adapted to engage one or more teeth and to be spaced from each other, each of said body members having a threaded bore therein, said threaded bores being oppositely threaded;
an elongated threaded member having externally threaded end portions which are oppositely threaded and which are engageable in said threaded bores of said body members to selectively expand or contract the spacing between said body members;
each of said body members having a first further bore therein which is laterally offset from said threaded bore, said first further bores having respective axes which are non-colinear with each other;
a first elongated member coupled to both of said body members and slideably engaged in said first further bore of said at least one body member and serving as a guide bar for said biassing device;
each of said body members having a second further bore therein which is laterally offset from said threaded bore and which is laterally offset from said first further bore, said second further bores having respective axes, said first and second further bores being located on the same side of said body member, all of said threaded bores and said first and second further bores having axes which lie substantially in a common plane, to permit substantially free access to said elongated threaded member over at least 180°; and
a second elongated member coupled to both of said body members and slideably engaged in said second further bore of at least one of said body mem- bers and serving as a second guide bar for said biassing device.

2. The biassing device of claim 1 further comprising first abutment means on at least one of said body members; and retaining means for selectively and abuttingly engaging with said first abutment means of at least one of said body members for positively preventing relative movement between said threaded members and said body members when the spacing between said body members is expanded to a predetermined spacing, thereby preventing disengagement of said threaded members from said body members.

3. The biassing device of claim 2 wherein said first abutment means is in communication with at least one of said threaded bore, first further bore and second further bore.

4. The biassing device of claim 2 wherein said retaining means comprises a projecting portion on at least one of said elongated threaded members, said first elongated member and said second elongated member.

5. The biassing device of claim 2 wherein said first abutment means comprises a smaller diameter portion at an end portion of at least one of said threaded bore, said first further bore and said second further bore.

6. The biassing device of claim 5 wherein said retaining means comprises an enlarged end portion of at least one of said elongated threaded member, first elongated member and second elongated member for abuttingly engaging said first abutment means.

7. The biassing device of claim 6 wherein said enlarged end portion comprises a washer-like member.

8. The biassing device of claim 6 wherein said enlarged end portion has an irregular surface portion.

9. The biassing device of claim 6 wherein said enlarged end portion comprises an outwardly flared end portion.

10. The biassing device of claim 9 wherein said outwardly flared end portion has a longitudinal slit in a portion thereof.

11. The biassing device of claim 1, 2 or 6 wherein at least one of said body members has a further abutment means at the end thereof opposite said first abutment means, said further abutment means being in communication with at least one of said threaded bore, first further bores and second further bores for abutting against at least one of said threaded member, first elongated member and second elongated member for preventing said member from extending outwardly of said at least one body member when the spacing between said body members is contracted.

12. The biassing device of claim 1 or 2 wherein said threaded bores in said first and second body members have axes which are non-colinear with each other.

13. The biassing device of claim 1 wherein the axes of said second further bores are non-colinear with each other.

14. In an orthodontic biassing device comprising:
two body members adapted to engage one or more teeth and to be spaced from each other, each of said body members having a threaded bore therein, said threaded bores being oppositely threaded;
an elongated threaded member having externally threaded end portions which are oppositely threaded and which are threadably engageable in said threaded bores of said body members to selectively expand or contract the spacing between said body members; and
means cooperatively coupled to said threaded member for preventing backing-off of said threaded member due to reaction forces applied to said body members when the spacing between said body members is expanded under the influence of said elongated threaded member, thereby causing said body members to remain at their relative expanded positions;
the improvement wherein:
said backing-off preventing means comprises a deformation in at least one of said threaded bores of said body members for frictionally engaging said elongated threaded member which is threadably engaged therein, said frictional engagement being such that said elongated threaded member is manually threadable in the expanding direction of said body members, but is substantially frictionally non-threadable in the contracting direction of said body members under the influence of reaction forces applied by the teeth to said body members.

15. The biassing device of claim 14 wherein said deformation comprises a deformation over substantially the complete length of said threaded bore.

16. The biassing device of claim 14 wherein said deformation is over a relatively small area of said threaded bore and located at the forward end of said threaded bore.

17. In an orthodontic biassing device comprising:
two body members adapted to engage one or more teeth and to be spaced from each other, each of said body members having a threaded bore therein, said threaded bores being oppositely threaded;
an elongated threaded member having externally threaded end portions which are oppositely threaded and which are threadably engageable in said threaded bores of said body members to selectively expand or contract the spacing between said body members; and
means cooperatively coupled to said threaded member for preventing backing-off of said threaded member due to reaction forces applied to said body members when the spacing between said body members is expanded under the influence of said elongated threaded member, thereby causing said body members to remain at their relative expanded positions;
the improvement wherein:
said backing-off preventing means comprises an enlarged end portion at at least one end of said elongated threaded member for frictionally engaging said threaded bore.

18. The biassing device of claim 17 wherein said enlarged end portion comprises a washer-like member secured to at least one end of said elongated threaded member.

19. The biassing device of claim 18 wherein said washer-like member has an irregular outer surface.

20. The biassing device of claim 18 wherein said washer-like member is eccentrically mounted relative to said elongated threaded member.

21. The biassing device of claim 17 wherein said enlarged end portion comprises an outwardly flared end portion.

22. The biassing device of claim 21 wherein said outwardly flared end portion has a longitudinal slit at an end portion thereof.

23. In an orthodontic biassing device comprising:

two body members adapted to engage one or more teeth and to be spaced from each other, each of said body members having a threaded bore therein, said threaded bores being oppositely threaded;

an elongated threaded member having externally threaded end portions which are oppositely threaded and which are threadably engageable in said threaded bores of said body members to selectively expand or contract the spacing between said body members; and means cooperatively coupled to said threaded member for preventing backing-off of said threaded member due to reaction forces applied to said body members when the spacing between said body members is expanded under the influence of said elongated threaded member, thereby causing said body members to remain at their relative expanded positions;

the improvement wherein:

said backing-off preventing means comprises a sleeve-like member engageable over said elongated threaded member and abutting against at least one of said body members for preventing backing-off of said threaded member.

24. The biassing device of claim 23 wherein said elongated threaded member has a spindle thereon, said sleeve-like member abutting against at least one of said body members and said spindle to prevent backing-off of said threaded member.

25. The biassing device of claim 23 or 24 wherein said sleeve-like member is made of resilient material and is snappable in place over said elongated threaded member.

26. The biassing device of claim 25 wherein said sleeve-like member has a re-entrant portion which is expandable to snappingly engage over said elongated threaded member.

27. An orthodontic biassing device comprising:

first and second body members adapted to engage one or more teeth and to be spaced from each other, each of said body members having a threaded bore therein, said threaded bores being oppositely threaded;

an elongated threaded member having externally threaded end portions which are oppositely threaded and which are threadably engageable in said threaded bores of said body members to selectively expand or contract the spacing between said body members;

at least one of said body members having a further elongated bore therein which is laterally offset from said threaded bore;

at least one elongated member coupled to both of said body members and slideably engaged in said further bore of said at least one body member; and said elongated member comprising backing-off preventing means cooperatively coupled with said at least one body member for preventing backing-off of said threaded member due to reaction forces applied to said body members when the spacing between said body members is expanded under the influence of said elongated threaded member, thereby causing said body members to remain at their relative expanded positions;

said backing-off preventing means comprising an enlarged end portion at at least one end of said elongated member for frictionally engaging an inner side wall of said further bore of said at least one body member with sufficient frictional force to substantially prevent backing-off of said threaded member due to reaction forces.

28. The biassing device of claim 27 wherein said enlarged end portion comprises a washer-like member at at least one end of said elongated threaded member.

29. The biassing device of claim 27 or 28 wherein said enlarged end portion has an irregular outer surface.

30. The biassing device of claim 28 wherein said washer-like member is eccentrically mounted relative to said elongated member.

31. The biassing device of claim 27 wherein said enlarged end portion comprises an outwardly flared end portion.

32. The biassing device of claim 31 wherein said outwardly flared end portion has a longitudinal slit at an end portion thereof.

33. An orthodontic biassing device comprising:

first and second body members adapted to engage one or more teeth and to be spaced from each other, each of said body members having a threaded bore therein, said threaded bores being oppositely threaded;

an elongated threaded member having externally threaded end portions which are oppositely threaded and which are threadably engageable in said threaded bores of said body members to selectively expand or contract the spacing between said body members;

at least one of said body members having a further elongated bore therein which is laterally offset from said threaded bore;

at least one elongated member coupled to both of said body members and slideably engaged in said further bore of said at least one body member; and said elongated member comprising backing-off preventing means cooperatively coupled with said at least one body member for preventing backing-off of said threaded member due to reaction forces applied to said body members when the spacing between said body members is expanded under the influence of said elongated threaded member, thereby causing said body members to remain at their relative expanded positions;

said elongated member having a roughened or serrated outer surface which frictionally bears against an inner surface portion of said further bore of said at least one body member.

34. An orthodontic biassing device comprising:

first and second body members adapted to engage one or more teeth and to be spaced from each other, each of said body members having a threaded bore therein, said threaded bores being oppositely threaded;

an elongated threaded member having externally threaded end portions which are oppositely threaded and which are threadably engageable in said threaded bores of said body members to selectively expand or contract the spacing between said body members;

at least one of said body members having a further elongated bore therein which is laterally offset from said threaded bore;

at least one elongated member coupled to both of said body members and slideably engaged in said further bore of said at least one body member; and said elongated member comprising backing-off preventing means cooperatively coupled with said at least one body member for preventing backing-off of said threaded member due to reaction forces applied to said body members when the spacing between said body members is expanded under the influence of said elongated threaded member, thereby causing said body members to remain at their relative expanded positions;

said elongated member having an irregular outer surface which frictionally bears against an inner surface portion of said further bore of said at least one body member.

35. The biassing device of claim 33 or 34 wherein said elongated member is a telescoping elongated member having at least one outer member and at least one inner member slidingly engaged therein, the outer surfaces of at least one of said inner and outer members being irregular to frictionally engage the inner surface of the other of said elongated members or of the inner surface of said at least one body member.

36. The biassing device of claim 35 wherein said inner and outer members are dimensioned relative to each other to provide a clearance therebetween, and said threaded member having a loose threaded engagement with the threads of said threaded bores into which it is threaded, to permit angulation of said inner and outer member relative to each other under the influence of said reaction forces.

37. The biassing device of claim 36 wherein said backing-off preventing means further comprises said elongated member being dimensioned relative to said further bore of said at least one body member to provide a clearance therebetween to permit said elongated member to angulate relative to said at least one body member to bind relative to said body member under the influence of said reaction forces.

38. An orthodontic biassing device comprising:
first and second body members adapted to engage one or more teeth and to be spaced from each other, each of said body members having a threaded bore therein, said threaded bores being oppositely threaded;
an elongated threaded member having externally threaded end portions which are oppositely threaded and which are threadably engageable in said threaded bores of said body members to selectively expand or contract the spacing between said body members;
at least one of said body members having a further elongated bore therein which is laterally offset from said threaded bore;
at least one elongated member coupled to both of said body members and slideably engaged in said further bore of said at least one body member; and
said elongated member comprising backing-off preventing means cooperatively coupled with said at least one body member for preventing backing-off of said threaded member due to reaction forces applied to said body members when the spacing between said body members is expanded under the influence of said elongated threaded member, thereby causing said body members to remain at their relative expanded positions;
said backing-off preventing means comprising a longitudinally distorted outer surface portion of said elongated member, said further bore being substantially straight.

39. The biassing device of claim 38 wherein said elongated member is wavy in the longitudinal direction thereof.

40. The biassing device of claim 39 wherein said elongated member is a telescoping member comprising at least one inner and outer members which are telescoping relative to each other, at least the inner member being wavy in the longitudinal direction thereof and the at least one outer member having an internal substantially straight bore for receiving said wavy inner member and for frictionally engaging said wavy inner member.

41. The biassing device of claim 40 wherein said inner and outer members are dimensioned relative to each other and to said further bores in said body members, and said threaded member having a loose threaded engagement with the threads of said threaded bores into which it is threaded, to permit relative angulation of said body members under the influence of said reaction forces to cause said elongated member to bind and prevent backing-off of said body members.

42. The biassing device of any one of claims 27, 33, 34 or 38, wherein said elongated member comprises at least first and second mutually telescoping elongated members, at least one of said mutually telescoping members being slideably received at least in said further bore of said at least one body member and being movable in the longitudinal direction thereof relative to both of said body members.

43. The biassing device of claim 42 wherein said elongated member comprises at least a first outer telescoping member and a first inner telescoping member, said outer telescoping member comprising retaining means cooperatively associated with said at least one body member for preventing disengagement thereof from said further bore of said at least one body member, and said inner elongated member comprising a retaining means cooperatively associated with said at least one outer telescoping member for engaging said at least one outer telescoping member to prevent disengagement between said inner and outer telescoping members.

44. The biassing device of claim 43 wherein said at least one body member comprises abutment means for preventing said outer telescoping member from extending outwardly from the rear end of said at least one body member, and said outer telescoping member comprising abutment means for abutting said inner telescoping member to prevent said inner telescoping member from passing outwardly through the rear of said outer telescoping member.

45. The biassing device of claim 42 wherein said elongated member comprises a common central member and a pair of further members telescopingly engaged at the ends of said central member, each of said further members being slideably engaged in a respective further bore of the respective one of said body members.

46. The biassing device of claim 45 wherein at least one of said body members comprises abutment means for abuttingly engaging said elongated member to prevent said elongated member from protruding from the rear end of said body member when the spacing between said body members is contracted.

47. The biassing device of claim 45 wherein said central member is an inner member, and said pair of further members are outer members telescopingly engaged at the ends of said inner member, said outer members having elongated bores therein for receiving said inner member, said elongated bores having abutment means for abuttingly engaging said inner member to prevent said inner member from protruding from the rear end of said outer members when said spacing between said body members is contracted.

48. In an orthodontic biassing device comprising:
two body members adapted to engage one or more teeth and to be spaced from each other, each of said body members having a threaded bore therein, said threaded bores being oppositely threaded;
an elongated threaded member having externally threaded end portions which are oppositely threaded and which are threadably engageable in said threaded bores of said body members to selectively expand or contract the spacing between said body members; and
means cooperatively coupled to said threaded member for preventing backing-off of said threaded member due to reaction forces applied to said body members when the spacing between said body members is expanded under the influence of said elongated threaded member, thereby causing said body members to remain at their relative expanded positions;
the improvement wherein:
said backing-off preventing means comprises said elongated threaded member having an outer threaded diameter which is threadably engaged in said threaded bore with a clearance therebetween to permit said elongated threaded member to angulate relative to said body members to bind relative to said body members under the influence of said reaction forces.

49. In an orthodontic biassing device comprising:
two body members adapted to engage one or more teeth and to be spaced from each other, each of said body members having a threaded bore therein, said threaded bores being oppositely threaded;
an elongated threaded member having externally threaded end portions which are oppositely threaded and which are threadably engageable in said threaded bores of said body members to selectively expand or contract the spacing between said body members; and
means cooperatively coupled to said threaded member for preventing backing-off of said threaded member due to reaction forces applied to said body members when the spacing between said body members is expanded under the influence of said elongated threaded member, thereby causing said body members to remain at their relative expanded positions;
the improvement wherein:
said backing-off preventing means comprises oversized threads on said elongated threaded member relative to the size of the threads of said threaded bore, whereby said elongated threaded member is manually rotatable in said threaded bores to expand the distance between said body members, but frictionally engages said threaded bore to prevent backing-off of said body members due to said reaction forces.

50. In an orthodontic biassing device comprising:
two body members adapted to engage one or more teeth and to be spaced from each other, each of said body members having a threaded bore therein, said threaded bores being oppositely threaded;
an elongated threaded member having externally threaded end portions which are oppositely threaded and which are threadably engageable in said threaded bores of said body members to selectively expand or contract the spacing between said body members; and
means cooperatively coupled to said threaded member for preventing backing-off of said threaded member due to reaction forces applied to said body members when the spacing between said body members is expanded under the influence of said elongated threaded member, thereby causing said body members to remain at their relative expanded positions;
the improvement wherein:
said elongated threaded member has threads of different size than the threads of said bores of said body members such that said elongated threaded member frictionally engages said threaded bores, but is manually rotatable relative to said body members in the expanding direction of said body members, but is frictionally retained to prevent backing-off of said threaded member due to said reaction forces.

51. An orthodontic biassing device comprising:
first and second body members adapted to engage one or more teeth and to be spaced from each other, each of said body members having a threaded bore therein, said threaded bores being oppositely threaded;
an elongated threaded member having externally threaded end portions which are oppositely threaded and which are threadably engageable in said threaded bores of said body members to selectively expand or contract the spacing between said body members;
at least one of said body members having a further elongated bore therein which is laterally offset from said threaded bore;
at least one elongated member coupled to both of said body members and slideably engaged in said further bore of said at least one body member; and
said elongated member comprising backing-off preventing means cooperatively coupled with said at least one body member for preventing backing-off of said threaded member due to reaction forces applied to said body members when the spacing between said body members is expanded under the influence of said elongated threaded member, thereby causing said body members to remain at their relative positions;
said backing-off preventing means comprising said elongated member being dimensioned relative to said further bore of said at least one body member to provide a clearance therebetween, and said threaded member having a loose threaded engagement with the threads of said threaded bores into which it is threaded, to permit said elongated member to angulate relative to said at least one body member to bind relative to said body member under the influence of said reaction forces.

* * * * *